US007751987B1

(12) United States Patent
Becker et al.

(10) Patent No.: US 7,751,987 B1
(45) Date of Patent: Jul. 6, 2010

(54) METHOD AND SYSTEM FOR PREDICTING AMINO ACID SEQUENCES COMPATIBLE WITH A SPECIFIED THREE DIMENSIONAL STRUCTURE

(75) Inventors: M. Oren Becker, Mevasseret Zion (IL); Maya Topf, Netanya (IL)

(73) Assignee: Ramot at Tel-Aviv University Ltd., Ramat-Aviv (IL)

( * ) Notice: Subject to any disclaimer, the term of this patent is extended or adjusted under 35 U.S.C. 154(b) by 673 days.

(21) Appl. No.: 09/718,425

(22) Filed: Nov. 24, 2000

(30) Foreign Application Priority Data

Aug. 16, 2000 (IL) .................................... 137886

(51) Int. Cl.
G06F 19/00 (2006.01)
(52) U.S. Cl. ...................................................... 702/27
(58) Field of Classification Search .................. 702/19, 702/20, 27, 22; 435/6, 69.1; 703/11
See application file for complete search history.

(56) References Cited

U.S. PATENT DOCUMENTS 5,600,571 A    2/1997   Friesner et al.

FOREIGN PATENT DOCUMENTS

WO    WO 98/47089    10/1998
WO    WO 01/37147     5/2001

OTHER PUBLICATIONS

Hurley, J. et al., Design and Structural Analysis of Alternative Hydrophobic Core Packing Arrang . . . , J. Mol. Biol. (1992), pp. 1143-1159.*
Dahiyat, B., et al., Protein design automation, (1996) Protein Science, Cambridge University Press.*
Bahar, I., et al., "Short-Range Conformational Energies, Secondary Structure Propensities, and Recognition of Correct Sequence-Structure Matches". Proteins: Structure, Function, and Genetics, 29:292-308 (1997).
Beauregard, M., et al., "Spectroscopic investigation of structure in octarellin (a de novo protein designed to adopt the α/β-barrel packing". Protein Engineering, 4:745-749 (1991).
Betz, Stephen F., et al., "Native-like and structurally characterized designed α-helical bundles". Current Opinion in Structural Biology, 5:457-463 (1995).
Bernstein, Frances C., et al., "The Protein Data Bank: A Computer-based Archival File for Macromolecular Structures". J. Mol. Biol., 112:535-542 (1977).
Betz, Stephen F., et al., "Controlling Topology and Native-like Behavior of de Novo-Designed Peptides: Design and Characterization of Antiparallel Four-Stranded Coiled Coils". Biochemistry, 35:6955-6962 (1996).
Brooks, Bernard R., et al., "CHARMM: A Program for Macromolecular Energy, Minimization, and Dynamics Calculations". Journal of Computational Chemistry, 4:187-217 (1983).
Connolly, Michael L., "Solvent-Accessible Surfaces of Proteins and Nucleic Acids". Science, 221: 709-713 (1983).

Dahiyat, Bassil I., et al., "Protein design automation". Protein Science, 5:895-903 (1996).
Dahiyat, Bassil I., et al., "Probing the role of packing specificity in protein design". Proc. Natl. Acad. Sci. USA, 94:10172-10177 (1997).
Desjarlais, John R., et al., "De novo design of the hydrophobic cores of proteins". Protein Science, 4:2006-2018 (1995).
Desmet, Johan, et al., "The dead-end elimination theorem and its use in protein side-chain positioning". Nature 356:539-542 (1992).
Fezoui, Youcef, et al., "De novo design and structural characterization of an α-helical hairpin peptide: A model system for the study of protein folding intermediates". Proc. Natl. Acad. Sci. USA, 91:3675-3679 (1994).
Harbury Pehr R., et al., "Repacking protein cores with backbone freedom: Structure prediction for coiled coils". Proc. Natl. Acad. Sci. USA, 92:8408-8412 (1995).
Hecht, Michael H., et al., "De Novo Design, Expression, and Characterization of Felix: A Four-Helix Bundle Protein of Native-Like Sequence". Science, 249:884-891 (1990).
Hellinga, Homme W., et al., "Constructions of New Ligand Binding Sites in Proteins of Known Structure". J. Mol. Biol., 222:763-785 (1991).
Herzyk, Pawel, et al., "A Reduced Representation of Proteins for Use in Restraint Satisfaction Calculations". Proteins: Structure, Function, and Genetics, 17:310-324 (1993).
Hurley, James H., et al., "Design and Structural Analysis of Alternative Hydrophobic Core Packing Arrangements in Bacteriophage T4 Lysozyme". J. Mol. Biol., 224:1143-1159 (1992).
Jones, David T., "De novo protein design using pairwise potentials and a genetic algorithm". Protein Science, 3:567-574 (1994).
Jorgensen, William L., et al., "Comparison of simple potential functions for simulating liquid water". J. Chem. Phys., 79:926-935 (1983).
Kamtekar, Satwik, et al., "Protein Design by Binary Patterning of Polar and Nonpolar Amino Acids". Science, 262:1680-1685 (1993).
Klemba, Michael, et al., "Novel metal-binding proteins by design". Structural Biology, 2:368-373 (1995).
Kono, Hidetoshi, et al., "Energy Minimization Method Using Automata Network for Sequence and Side-Chain Conformation prediction From Given Backbone Geometry". Proteins: Structure, Functions, and Genetics, 19:244-255 (1994).
Kortemme, Tanja, et al., "Design of a 20-Amino Acid, Three-Stranded β-Sheet Protein". Science, 281:253-256 (1998).

(Continued)

Primary Examiner—Jerry Lin
(74) Attorney, Agent, or Firm—The Nath Law Group; Susanne M. Hopkins; Ari G. Zytcer

(57) ABSTRACT

A method for predicting an amino acid sequence compatible with a three-dimensional (3D) structure of a protein. A reduced virtual representation of the 3D structure is constructed, and, for each position along the representation, its solvent accessibility is determined. For each position along the structure, an amino acid residue is randomly selected from a predefined group of amino acids having a solvent accessibility compatible with the solvent accessibility of the position. A Monte-Carlo simulation is performed on this devised protein in which an amino acid at a particular position is sequentially replaced with other amino acids having the same solvent accessibility, and an energy score is calculated for each rotamer. The lowest scoring rotamer for this position is then selected The Monte-Carlo simulation is repeated for each position along the sequence, to obtain an amino acid sequence with the lowest total energy score.

21 Claims, 7 Drawing Sheets

OTHER PUBLICATIONS

Kuroda, Yutaka, et al., "Solution Structure of a de Novo Helical Protein by 2D-NMR Spectroscopy". J. Mol. Biol., 236: 862-868 (1994).

Lau, Kit Fun, et al., "Theory for protein mutability and biogenesis". Proc. Natl. Acad. Sci. USA, 87:638-642 (1990).

Lazar, Greg A., et al., "De novo design of the hydrophobic core of ubiquitin". Protein Science, 6:1167-1178 (1997).

MacKerell, A. D., Jr., et al., "All-Atom Empirical potential for Molecular Modeling and Dynamics Studies of Proteins". J. Phys. Chem. B, 102:2586-3616 (1998).

Malakauskas, Sandra M., et al., "Design, structure and stability of a hyperthermophilic protein variant". Nature Structural Biology, 5:470-475 (1998).

Metropolis, Nicholas, et al., "The Monte Carlo Method". Journal of the American Statistical Association, 247:335-341 (1949).

Miyazawa, Sanzo, et al., "Residue-Residue Potentials with a Favorable Contact Pair Term and an Unfavorable High Packing Density Term, for Simulation and Threading". J. Mol. Biol., 256:623-644 (1996).

Nautiyal, Shivani, et al., "A Designed Heterotrimeric Coiled Coil". Biochemistry, 34:11645-11651 (1995).

Pveletich, Nikola P., et al., "Zinc Finger-DNA Recognition: Crystal Structure of a Zif268-DNA Complex at 2.1 Å". Science, 252:809-817 (1991).

Ponder, Jay W., et al., "Use of Packing Criteria in the Enumeration of Allowed Sequences for Different Structural Classes". J. Mol. Biol., 193:775-791 (1987).

Quinn, Thomas P., et al., Betadoublet: De novo design, synthesis, and characterization of a β-sandwich protein. Proc. Natl. Acad. Sci. USA, 91:8747-8751 (1994).

Raleigh, Daniel P., et al., "A de Novo designed Protein Mimics the Native State of Natural Proteins". J. Am. Chem. Soc., 117:7558-7559 (1995).

Regan, Lynne, et al., "Characterization of a Helical protein designed from First Principles". Science, 247:976-978 (1988).

Rost, Burkhard, et al., "Prediction of protein Secondary Structure at Better than 70% Accuracy". J. Mol. Biol., 232:584-599 (1993).

Salamov, Asaf A. et al., "Prediction of Protein Secondary Structure by Combining Nearest-neighbor Algorithms and Multiple Sequence Alignments" J. Mol. Biol., 247:11-15 (1995).

van Gunsteren, W. F., et al., "Algorithms for macromolecular dynamics and constraint dynamics". Molecular Physics, 34:1311-1327 (1977).

Raha, Kaushik, et al., "Prediction of amino acid sequence from structure". Protein Science, 9: 1106-1119, 2000.

Dahiyat, Bassil I., et al., "De Novo Protein Design: Fully Automated Sequence Selection". Science, vol. 278, pp. 82-87, Oct. 3, 1997.

Olszewski, Krzysztof A., et al., "Folding Simulation and Computer Redesign of Protein A Three-Helix Bundle Motifs". Proteins: Structure, Function, and Genetics 25:286-299 (1996).

* cited by examiner

METHOD AND SYSTEM FOR PREDICTING AMINO ACID SEQUENCES COMPATIBLE WITH A SPECIFIED THREE DIMENSIONAL STRUCTURE

FIELD OF THE INVENTION

This invention relates to the field of protein design and more particularly to the field of inverse-protein folding for de novo protein design.

PRIOR ART

The following is a list of prior art which is considered to be pertinent for describing the state of the art in the field of the invention. Acknowledgement of these references herein will be made by indicating the number from their list below within brackets.
1. Desjarlais J. R. & Handel T. M. *Protein Science* 4:2006-2018 (1995).
2. Lazar G. A. et al. *Protein Sci.* 6:1167-1178 (1997).
3. Hellinga H. W. et al. *J. Mol. Biol.* 222:763-785 (1991).
4. Hurley H. W. et al. *J. Mol. Biol.* 224:1143-1154 (1992).
5. Harbury P. B. et al. *PNAS USA* 92:8408-8412 (1995).
6. Klemba M. et al. *Nat. Struc. Biol.* 2:368-373 (1995).
7. Nautiyal S. et al. *Biochemistry* 34:11645-11651 (1995).
8. Betz S. F. et al. *Biochemistry* 35:6955-6962 (1996).
9. Dahiyat B. I. et al. *Protein Science* 5:895-903 (1996).
10. Jones D. T. et al. *Protein Science* 3:567-574 (1994).
11. Kono H & Doi J. *Proteins: Structure, Function and Genetics* 19:224-255 (1994).
12. Desmet J. et al. *Nature* 356:539-542 (1992).
13. Dahiyat B. I. & Mayo S. L. *Protein Sci.* 5:895-903 (1997).
14. Dahiyat B. I. & Mayo S. L. *Proc. Natl. Acad. Sci. USA* 94:10172-10177 (14987).
15. Malakauskas S. M. and Mayo S. L. *Nat. Struct. Biol.* 5:470-475 (1998).

BACKGROUND OF THE INVENTION

Depending on the primary structure and the environment, proteins fold into a three-dimensional (3D) structure containing recurring motives which pack together to form the 3D structure, the most common motives observed being the α-helix, β-turn, parallel and anti-parallel β-sheets.

The 3D structure of a protein may be characterized as having internal surfaces being the areas buried within the structure and thus directed away from the aqueous environment in which the protein is normally found; external surfaces being the areas exposed to the aqueous environment and intermediate or boundary surfaces. Through the study of many natural proteins, researches have discovered that hydrophobic residues are most frequently found on the internal surface of water soluble protein molecules while hydrophilic residues are most frequently found on the external protein surfaces.

It was established that while the biological properties of a protein depend directly on the protein's 3D conformation, only some of the information in the protein's sequence is necessary to specify its fold, i.e. a given native structure may be formed from many different sequences [Lau K. F. and Dill K. A. PNAS USA 87:638-652 (1990)]. The different sequences compatible with a given 3D structure are referred to as the structure's Sequence Space. The finding that a number of amino acid sequences may fold into the same basic 3D structure, have focused attention on a new field commonly referred to as the "inverse protein folding" or "de novo protein design". While conventional protein folding methods are trying to predict the tertiary structure of a protein from their amino acids sequence, protein design methods are looking for a sequence that will stabilize a given fold, by using the same principals.

Reports of experimentally predicted amino acid sequences which adopt an intended fold and possess physical properties similar at least in part to those of natural proteins are appearing with increasing frequency [Kortemme T. et al. *Science* 281:253-256 (1998); Kurda Y. et al. *J. Mol. Biol.* 236:862-868 (1994); Quinn T. P. et al *PNAS USA* 91:8747-8751 (1994); Fezoui, Y. et al *PNAS USA* 91:3675-3679 (1994); Betz S. F et al *Curr. Opin. Struc. Biol.* 5:457-463 (1995); Raleigh D. P. et al *J. Am. Chem. Soc.* 117:755-7559 (1995); Regan L. & DeGardo W. F. *Science* 241:976-978 (1988); Hecht M. H. et al. *Science* 249:884-891; Beauregard M. et al. *Protein Eng.* 4:745-749 (1991) Kamtekar S. et al *Science* 262:1680-1685 (1993)]. These studies have been predominantly experimental and rely on knowledge of the physical properties that determine the protein's structure, such as the patterns of hydrophobic and hydrophilic residues in the sequence.

Several groups have applied an experimentally tested systematic, quantitative methods to protein design with the goal of developing general design algorithms. Desjarlais and Handel [1] were the first to experimentally investigate predictions generated by genetic algorithms (GA). They have developed ROC ("Repacking of Cores"), a computational program that attempts to find novel core sequences given the backbone structure of the protein of interest. In different, however related, work, a modification of the ROC was used on the secondary structure of the αβ protein ubiquitin[2]. The program used a genetic algorithm to optimize the search for alternative core structures for a given protein. Other experimentally tested methods applied with respect to protein design are described elsewhere[3-11]. Thus, in some cases, uniquely folded and even functional globular proteins may be obtained using highly simplified minimally designed cores. The algorithms consider the spatial positioning and steric complement of side chains by explicitly modeling the atoms of sequences under consideration. However, despite the success of these studies, a full predictive understanding of hydrophobic core packing in proteins has not yet been fully realized, and de novo design of stable and unique proteins, remains a challenging problem.

A major breakthrough was achieved by the Dead-End Elimination (DEE) algorithm by Desmet et al.[12], which was originally developed for homology modeling. DEE finds and eliminates rotamers that are mathematically provable to be inconsistent (or dead ending) with the global minimum energy solution of the system.

Dahiyat and Mayo[12] further adapted the algorithm by Desmet for the explicit exploration of sequence space using semi-empirical potential functions and stereochemical constraints, which intended to capture most of the known contributions of protein stability. In their design strategy they succeeded in expanding the range of computational protein design to residues of all parts of the protein: the buried core, the solvent-exposed surface, and the boundary between core and surface.

SUMMARY OF THE INVENTION

In accordance with a first of its aspects, the present invention relates to a computer-implemented method for predicting at least one amino acid sequence compatible with a predefined three-dimensional (3D) structure, which method comprises the steps of:

a) providing a coordinate set representing the backbone of said 3D structure;

b) constructing a reduced virtual representation for the 3D structure provided in step (a);

c) determining for each position along the virtual structure representation provided in step (b) its solvent accessibility;

d) constructing an initial amino acid sequence by assigning each position along the sequence an amino acid residue selected randomly from a predefined group of amino acids having a solvent accessibility (SA) compatible with the solvent accessibility determined for each position;

e) randomly selecting one or more positions along the sequence provided in step (d) and applying on each position a Monte-Carlo simulation in sequence space and rotamer space, said simulation comprising one or more scoring function calculating steps which include:

i) randomly selecting one or more amino acid residues of the same solvent accessibility as that defined for said position to provide a mutation;

ii) calculating an energy scoring function for each possible rotamer of each amino acid residue provided in step (i) based on their said reduced virtual representation;

iii) selecting the lowest scoring rotamer or when more than one amino acid is manipulated simultaneously, selecting the lowest scoring rotamer combination;

iv) determining whether to accept or reject the mutation with the rotamer or rotamer combination selected in step (iii), by applying, for example, the Metropolis algorithm; and v) assigning the amino acid residue or residues and their respective selected rotamer or rotamer combinations selected in step (iii) to said position/s and moving to another position along the sequence;

said simulation steps are repeated until for each position along said sequence, the residue and residue's rotamer with the lowest score is selected, to obtain a virtually represented amino acid sequence with the lowest total score;

f) expanding the reduced representation of the amino acid sequence obtained in step (e) to its corresponding all-atom sequence representation thereby obtaining an amino acid sequence compatible with said predefined 3D structure; and g) optionally, creating a computer output of the expanded all-atom representation of the amino acid sequence obtained in step (f).

According to a second aspect, the invention provides amino acid sequences which fold into predefined 3D structures, the amino acid sequences being obtained by the method of the present invention.

Furthermore, the invention provides, in accordance with another of its aspects, a computer-based system for predicting an amino acid sequence compatible with a predefined 3D structure comprising a computer device equipped with: (a) input apparatus, such as a keyboard, for specifying said 3D structure; (b) a first memory for storing the specified 3D structure; (c) a second memory having a stored thereon an application program which when running, provides at least one amino acid sequence compatible with the specified 3D structure; (d) a third memory for storing the at least one amino acid sequence obtained; (e) a processor coupled to said input means, and to said first, second and third memories for representation of said amino acid sequence; and (f) optionally, a display unit coupled to said processing means for displaying the amino acid sequence.

The specified 3D structure may be obtained from a data bank accessible through the network or available on diskette, CD or tape which is then downloaded onto the first memory module. Thus, the term "input apparatus" signifies also any suitable means for connecting to a network and retrieving from available databanks accessible thereby the desired 3D structure. Furthermore, input apparatus also refers to any apparatus enabling retrieving such sequences from computer readable mediums, e.g. diskettes, CDs, tapes etc.

The processor may be any computer device stored with an application utility, which when running on the computer device, enables the processing of the stored data so as to provide a an amino acid sequence which substantially folds into a desired 3D structure, i.e. that specified in step (a) of the method of the invention, such a computer device includes, inter alia, a private computer (PC, either Windows or Linux OS), workstation computers (UNIX), a computer-cluster or Super-computers.

BRIEF DESCRIPTION OF THE DRAWINGS

In order to understand the invention and to see how it may be carried out in practice, some non-limiting examples will now be described, with reference to the accompanying drawings, in which.

DETAILED DESCRIPTION OF THE INVENTION

Figure 1:
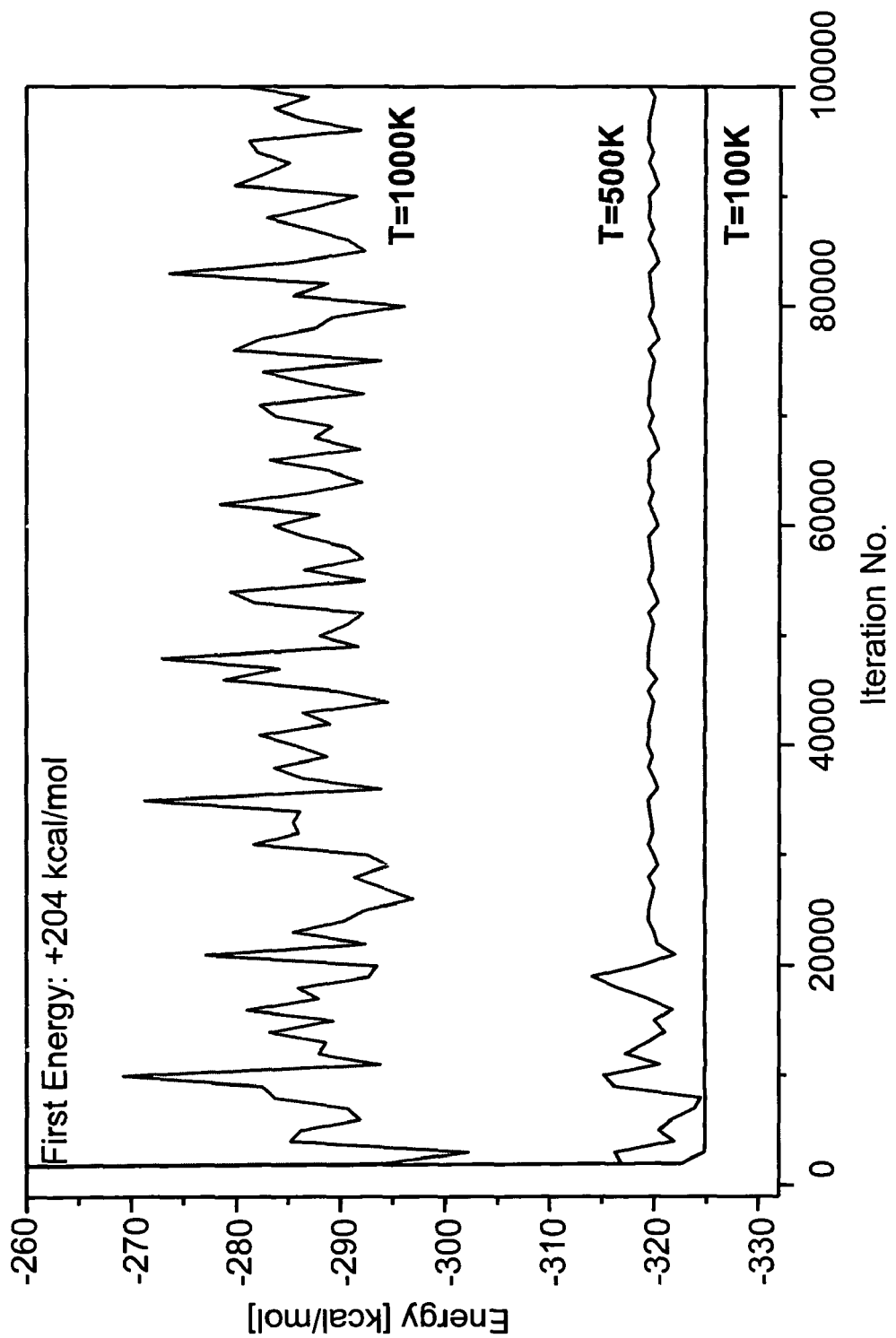
FIG. 1 shows the energy profile obtained for the Zin268 backbone by the system of the invention, during $10^5$ iterations, at three temperatures: 1000K (continuous line), 500K (broken line) and 100K (dotted line). The temperature remained constant during the simulation. The energy of the initial random sequence, before simulation initiated was +204 kcal/mol.

The present invention relates in general to a method of predicting one or more amino acids compatible with a predefined 3D structure. The predefined 3D structure may be that of a native protein, polypeptide, a biologically functional derivative or fraction of the native protein or polypeptide or any other biologically functional polymer, the determination of its lowest free-energy-structure is desirable.

In the current disclosure, above and below, the terms "amino acid sequence", "primary sequence" and other similar terms or derivation thereof, may be used interchangeably. These terms, as used herein, refer to an amino acid sequence of a protein or polypeptide. The primary structure of a protein or polypeptide is the amino acid sequence wherein the location of disulfide bridges, if any exist, are indicated. The primary structure is thus a complete description of the covalent connections within the polymer.

The terms "Zif268" and "SEQ. ID NO. 1" are used interchangeably herein.

The terms "FSD-1" and "SEQ. ID NO. 2" are used interchangeably herein.

The terms "sequence A" and "SEQ. ID NO. 3" are used interchangeably herein.

The terms "sequence B" and "SEQ. ID NO. 4" are used interchangeably herein.

The terms "Gβ1" and "SEQ. ID NO. 5" are used interchangeably herein.

The terms "sequence C" and "SEQ. ID NO. 6" are used interchangeably herein.

The terms "sequence D" and "SEQ. ID NO. 7" are used interchangeably herein.

The terms "Gβ1-c3b4" and "SEQ. ID NO. 8" are used interchangeably herein.

The term "amino acid" as used herein above and below means any organic compound possessing one or more amino groups and one or more carboxyl groups. Such amino acids may be naturally occurring L-amino acids, their corresponding D-isomers, synthetic amino acids, or any other variations of the same. Within this context, the term variant should be understood as including all possible modifications of the naturally occurring or synthetic amino acids including deletions, insertions, substitutions of group/s therein. By the term "amino acid residue", it should be understood an amino acid, as defined above, which forms part of a chain, the chain consisting two or more amino acid units.

The coordinate set including the dihedral angles and specific bonds within the predefined 3D structure, may be obtained from any suitable databank known to those versed in the art, such as the Protein Data Bank (PDB, supported by the RCSB consortium) and is preferably provided in a computer readable form to enable its easy input into the system of the invention. Alternatively, the 3D structure may be defined at will, without relying on any known 3D structure of any specific protein. Such novel 3D structures will agree with the general structure constraints of polypeptides, such as backbone geometries, as known to those versed in the art.

According to the method of the invention, a reduced virtual representation is first constructed for the predetermined 3D structure. The reduced representation may be obtained by the methodology originally developed by Herzyk and Hubbard for use with dynamic simulated annealing [Herzyk P. and Hubbard R. E. Proteins 17:310-324 (1993)]. According to this methodology, the amino acids are represented by virtual spherical atoms, wherein the main chain of the protein, polypeptide or any other suitable polymer is represented by one virtual atom per residue located at the Cα position and the side chains are represented by one or more additional virtual atoms. The number of additional virtual atoms depends on the size and chemical composition of the specific side chain.

In the 'reduced representation' disclosed in the Herzyk et al reference, each amino acid residue is represented by one or more spheres, and at least one amino acid is represented by two or more spheres. The virtual bonds and excluded volume of these atoms were parameterized by analysis of 83 protein structures determined by x-ray crystallography. The authors used this representation in restraint satisfaction calculation with dynamic simulated annealing in the context of NOE distance constraints. They compared the results obtained with this reduced representation to previous results obtained using an all-atom representation for the determination of the structure of crambin, echistatin and protein G from their experimental NOE data. They found that their 'reduced representation' permitted a 30-fold decrease in computer time for generating a single structural solution, and a 20-fold decrease in computer time to produce an acceptable structure, compared to the use of an all-atom model. The RMS distances between the reduced representation model and the all atom model were 1.5 A to 1.7 A.

Typically, one additional virtual atom will represent amino acid residues having only a β side chain heavy atom or β and γ side chains heavy atoms, e.g. serine (Ser, S), threonine (Thr, T), alanine (Ala, A), valine (Val, V), cysteine (Cys, C). Proline will also consist part of this group as its Cδ heavy atom is very close to its Cα and Cβ atoms. Two additional virtual atoms will represent amino acid residues having β, γ and δ side chains heavy atoms, β being represented by one virtual atom and γ and δ together by another virtual atom. It should be noted that the representation with two additional side chain virtual atoms exhibit rotational flexibility around the Cβ-Cγ bond, e.g. histidine (His, H), aspartic acid (Asp, D), asparagine (Asn, N), tyrosine (Tyr, Y), leucine (Leu, L), isoleucine (Ile, I), phenylalanine (Phe, F) and methionine (Met, M). Three additional virtual atoms will represent amino acid such as lysine (Lys, L), arginine (Arg, R), glutamic acid (Glu, E), Glutamine (Gln, Q) and tryptophane (Trp, W). Evidently, amino acids, other than the naturally occurring amino acids (e.g. chemical modifications or synthetic variations thereof) may be presented by virtual atoms in a similar manner.

After constructing the reduced representation for the 3D structure provided, the extent of solvent accessibility at each position along the 3D structure is determined. In principal, solvent accessibility (SA) is a feature assigned for each position along the chain of the folded protein or polypeptide. Each position is categorized as being either buried within the 3D structure (in an internal surface), exposed (part of an external surface) or within a boundary surface (intermediate position).

According to one preferred embodiment of the invention, the SA is determined by surrounding the reduced representation of the protein with a grid and calculating the number of grid points that fall into the intersection volume of the volume of every virtual atom and the volume of its neighbor virtual atom (the volume determined according to the adequate van der Waals radius [Bernstein F. C. et al. J. Mol. Biol. 112:535-542 (1977)]. However, it should be clear that other ways of determining an amino acid's SA can be employed as may be known to the man versed in the art.

Each type of position, i.e. buried, exposed or intermediate, may be occupied by several amino acid residues. Hydrophobic amino acids, being able to form a hydrophobic core, are assigned to the buried positions of the 3D structure, while hydrophilic amino acids are assigned for the solvent-exposed positions. Boundary positions, between those two environments can be occupied by both types of amino acids.

According to one particular embodiment of the invention, the buried positions may be occupies by amino acids selected from the group consisting of Ala, Tyr, Trp, Val, Leu, Ile, Phe, Met, Cys, Pro, Gly and variants thereof, all of which being hydrophobic in nature.

The exposed positions may be occupied by amino acid residues selected from the group consisting of Lys, Arg, His, Glu, Asp, Gln, Asn, Ser, Thr and variants thereof all of which being hydrophilic in nature.

The positions having assigned an intermediate level of SA, may be occupied by all types of amino acids, particularly those which serve in nature as building blocks for proteins, i.e. Pro, Lys, Arg, His, Glu, Asp, Gln, Asn, Ser, Thr, Gly, Ala, Tyr, Trp, Val, Leu, Ile, Phe, Met, Cys and variants thereof.

It should be noted, however, that the above classification of the buried, intermediate and exposed residues is only one example of classification and these groups may be changes.

Special assignment of patterns may be set for particular positions in the protein's 3D structure that deviate from the general assignment based on SA, such assignment may be introduced, for example, to preserve buried salt bridges.

After assigning each position with its characteristic SA (1) an amino acid for every Cα position is selected randomly, taking into account the solvent accessibility of that position (buried, exposed or intermediate). Alternatively, this selection may be applied only to a sub-set of the polypeptide's amino acid residue, leaving the other positions fixed throughout the design process; (2) the appropriate bonds and angles of the protein's reduced representation are assigned based on the coordinate set provided; and (3) one of the physically permissible rotamers that characterizes each of the amino acids is assigned.

A scoring function is applied to evaluate the effect of changing the amino acid sequence and residue rotamer for a given 3D backbone structure. The scoring function used according to the present invention has two main contributions: a residue-residue interaction term and a residue's secondary-structure propensity term. The interaction part of the scoring function is based in part on the Lenard-Jones like potential function, multiplied by the effective attractive inter-residue contact energies ($\epsilon i,j$). The energy is summed over all possible pairs of residues in the protein where the energy between each pair residues is a sum of the interaction energies between all possible pairs of virtual atoms except for the energy between two neighboring Cα virtual atoms that do not contribute to the interaction. Since each side chain is represented by one or more virtual atoms, the energy contribution of each residue-residue pair is divided among the virtual atoms such that the sum over energy contributions of the virtual atom pairs (one from each residue) equals the effective residue-residue interaction. The Lenard-Jones potential function is modified to make the effect of repulsion smaller (because the virtual atoms are 'softer' than real atoms).

The effective contact energies between two amino acids may be, for example, those calculated by Miyazawa and Jernigan [Miyazawa S. and Jernigan R. L. J. Mol. Biol. 256: 623-644 (1996)]. The basic assumption on which the contact energies are calculated according to this model is that the average characteristics of residue-residue contacts, observed in a large number of crystal structures of globular proteins, represents the actual intrinsic inter-residue close contacts of protein structures.

Secondary structure propensities are also included in the scoring function. To this end, the total energy score of the protein is calculated by adding a residue specific "potential" for α-helical and β sheet states. These terms may be, for example, those calculated by Bahar et al. [Bahar I. et al. Proteins 29:292-308 (1997)]. These so-called potentials are added only if the residue is situated in a α-helical or a β-sheet regions of the 3D backbone template, according to the secondary structure of the designed protein or polypeptide.

The scoring function is applied as part of a Monte Carlo simulation which combines a search in the sequence space for amino acid residues and in the specific rotamer space of each residue. This process provides the system with the optimal sequence for a given backbone. The term "optimal sequence" refers to an amino acid sequence compatible with the pre-defined 3D structure and having the lowest total score.

The term "Sequence space" refers to the total number of possible different sequences for a given number of different residues and a given number of residues in the protein, polypeptide or any other appropriate polymer, e.g. for a protein of 100 residues, composed of 20 different amino acids, the sequence space will contain $20^{100}$ possible sequences. The term "Rotamer space" refers to the total number of physically permissible conformations for a residue in a given amino acid sequence.

The advantage of the combined reduced representation of the side chains and the grouping of amino acids and structure sites according to the solvent accessibility relies in the high efficiency of searching through both sequence space and rotamer space. The combined simplifications, dramatically reduce the search space, while retaining a physically reasonable representation that can accurately account for rotamer flexibility.

The search in sequence space begins when up to three positions along the protein are simultaneously randomly selected and replaced with different amino acids (each replacement referred to as a 'mutant' in that specific 'trial configuration'). The replacing amino acids are selected randomly from the group of amino acids having the same characteristics (buried, exposed or intermediate) as defined for the specific replaced positions to form the 'mutant'. If any of the new mutation residues has more than one virtual side chain atom, a search in rotamer space begins by calculating the total energy score of the new sequence for each and every allowed rotamers or rotamer combinations of the mutated amino acids (not all rotamers are allowed, as described by Ponder and Richards [Ponder J. W. and Richards F. M. J. Mol. Biol. 193(4):775-791 (1987)]. The energy score difference $\Delta E$, between the lowest energy score of the trail configuration being the lowest energy score among all allowed rotamers of the new mutant (or mutants, if more than one amino acid is replaced), and the energy of the last accepted configuration is calculated. The Metropolis algorithm [Metropolis N. & Ulam S. J. Am. Stat. Ass. 44:335-341 (1949)] is used to determine whether the new trial sequence is accepted or rejected. If $\Delta E$ is negative, the mutation is accepted with the best rotamers, otherwise, the trial configuration is accepted at a probability determined according to the Boltzmann distribution $\epsilon^{-\Delta E/RT}$ (T being either a fixed or a varying annealing temperature as will be described hereinbelow).

The search continues through a large number of trials (steps) in order to allow the score to decrease and converge. This number depends on the size of the protein and on the number of residues that are allowed to be mutated (in case the design is just of a certain part of the protein).

It is possible to perform multiple mutations in each simulation step with adjustable probabilities to determine whether one or more mutations take place at any given trial step. If two or more mutations take place simultaneously, the minimal energy score among all rotamer combinations of those mutations in the new sequence that has side chains of two or more virtual atoms, is searched.

Throughout the simulation, the lowest "scored" sequences are selected. The final optimal sequence is the one associated with the lowest total energy score found during the optimization process. The resulting sequence is then expanded to its corresponding 3D all-atom representation (as opposed to the virtual representation). This all atom representation may then be either saved in a computer readable form or extracted in the form of a computer output. Also collected are additional low energy score sequences, in order to enable analyzing relative consistency patterns of residues in a given position.

To evaluate whether the sequence obtained is indeed compatible with the predefined 3D structure, the all atom 3D model that is constructed from the novel sequence can be analyzed. There are several methods for determining whether a designed amino acid sequence indeed folds into a predefined 3D structure. One way of performing such an evaluation is to compare the structure of the designed protein (after standard all-atom minimization of its side chains) with the structure of the model after molecular dynamics simulation in water or by comparing the molecular mechanics energy of the wild-type protein from which the 3D structure used, was taken, with that of the designed protein, after molecular dynamics of the latter. Molecular dynamics programs, such as CHARMM [Brooks, B. R. et al. *J. Comp. Chem.* 4:187-219 (1983)] may be utilized for this purpose, as illustrated in the following Examples.

The amino acid sequence designed by the method of the invention is a de novo sequence and preferably a sequence, which under physiological conditions folds substantially into the desired 3D structure. More preferably, the amino acid sequences obtained are biologically functional.

The sequence obtained may be used for various applications. According to one preferred embodiment, the designed amino acid sequence is chemically synthesized by procedures known in the art.

In a further preferred embodiment, the novel amino acid sequence is used to create a nucleic acid sequence, such as DNA, which encodes the optimal sequence. A man versed in the art would know based on the existing technologies how to deduce at least one nucleic acid which will encode the amino acid sequence designed. The nucleic acid sequence obtained may then be cloned into a host cell and expressed. The choice of codons, suitable expression vectors and suitable host cells may vary depending on a number of factors, and can be easily optimized as needed.

Once made, the novel amino acid sequence may be experimentally evaluated and tested for structure, function and stability, as required. This will be performed as is known in the art and will depend in part on the original protein from which the sequence's backbone structure was taken. Preferably, the designed protein will be more stable than the known protein used as the starting point, although, at times, if some constraints are placed on the method disclosed herein, the designed sequence may be less stable. For example, it is possible to fix certain residues for altered biological activity and find the most stable sequence, but it may still be less stable than the wild type protein. Stable in this context includes, but is not limited thereto, thermal stability, i.e. an increase in the temperature at which reversible or irreversible denaturing starts to occur; proteolytic stability, i.e. decrease in the amount of protein which is irreversibly cleaved in the presence of a particular protease (including autolysis); stability to alteration in pH or oxidative conditions; chelator stability; stability to metal ions; stability to solvents such as organic solvents, surfactants, formulation chemicals, etc.

The proteins of the invention, and naturally, the nucleic acid deduced therefrom, may be used in a variety of applications, ranging from industrial to pharmacological uses, depending on the protein. Example of the different uses are in biotechnology manufacturing of therapeutic peptides and proteins, in gene therapy, design of modified therapeutic peptides and proteins as pharmaceuticals, etc.

Another application of the invention disclosed herein may be the generation of a library of small stable protein elements that can be later assembled in various ways to design a sequence for a novel larger protein with a desired 3D structure. Yet further, the method of the present invention may be applicable for optimizing the novel larger protein obtained thus ensuring that the peptides from which it was constructed indeed fit the structure.

In view of the above, the invention further provides amino acid sequences substantially compatible with a specified 3D structure, the amino acid sequences being obtained by the method of the present invention.

Yet further, in accordance with another of its aspect, there is provided a computer-based system for predicting an amino acid sequence compatible with a specified 3D structure, the system comprising the constituents as defined hereinbefore and after.

The input apparatus, such as a keyboard, employed by the system of the invention, are used for entering a selected set of coordinates representing the predefined 3D structure and other data such as scoring function and optimization process parameters. The first and third memory means being preferably a RAM (random access memory) are used for storing the initial and final data while the second memory means, being preferably a ROM (read-only memory) are used to store the program of the method of present invention. Further, the system comprises a microprocessor for performing, under control of the stored program, the steps of processing the entered data and displaying via a display unit or printer the novel amino acid sequence.

A user enters the coordinate set for the predefined 3D structure from an optional, auxiliary storage unit. In response to entry of the coordinate set, the system inputs the data for processing, stores the data in memory then processes it as described. The data provided regarding the 3D structures is typically retrieved from existing files known to those versed in the art and available to them.

SPECIFIC EXAMPLES

The present invention is defined by the claims, the contents of which are to be read as included within the disclosure of the specification, and will now be described by way of example with reference to the accompanying Figures.

GENERAL

CHARMM Minimization and Molecular Dynamics

The comparison between the all-atom 3D structure of the designed protein (after minimization of its side chains) with its structure after molecular dynamics simulation is carried out in the following specific Examples using the CHARMM molecular dynamics program [version 29, Brooks B. R. et al. (1983) ibid.]. Further, the comparison between the averaged energy of the designed protein after dynamics with the energy of the native protein is carried out using CHARMM forcefield

[Mackerell A. D. et al. *J. Phys. Chem.* 102:3586-3616 (1998)]. The minimization and the molecular dynamics are performed when the protein is embedded in a water sphere. For native proteins, the coordinates are based on the information provided from PDB. The conformation of the designed protein is composed of the backbone conformation of the native protein and the side chains conformation of the new residues, according to the best rotamers chosen by the method of the invention.

CHARMM executes two minimization algorithms to the protein's side chains, Steepest Descent (SD) and Adopted Basis Newton Raphson (ABNR). After the minimization of the side chains and of the water surrounding the protein, CHARMM performs molecular dynamics of the protein.

Example 1

Zif268 as a Target Fold

In order to examine the method according to the invention the ββα motif typified by the zinc finger DNA binding module in the zinc finger protein, Zif268 was used. Zif268 is a well recognized protein which has the sequence shown in SEQ. ID NO. 1. This protein is small enough to be both computationally and experimentally retractable, yet large enough to form an independently folded structure in the absence of disulfide bonds or metal binding. Although this motif consists of fewer than 30 residues, it does contain sheet, helix and turn structures. By the method and system of the invention the entire amino acid sequence: the buried core, the solvent exposed surface and the boundary between core and surface, except for the Gly27, which was not mutated during the simulation, was computed. The input coordinates are those of residues 33-60 of the native proteins obtained from the X-ray structure coordinate of Zif268 immediate early gene (krox-24) complex with an 11 base pair DNA fragment (Protein Data Bank (PDB) code: 1ZAA), as determined at 2.1 Å resolution by Pavletich and Pabo [Pavletich N. P., Pabo Science 252:809-817 (1991)]. Recently, this protein was also analyzed by Dahiyat & Mayo (13).

1.1 Solvent Accessibility of Zif268

Solvent accessibility (SA) was determined based on the coordinates of the native protein and each residue along the chain was assigned a level of SA-buried, -exposed or -intermediate. Table 16 presents a comparison between the SA obtained according to one embodiment of the present the invention and those obtained by Dahiyat and Mayo[13].

(1983)] with subsequent manual changes in SA assignment of positions 1, 17 and 23 from the boundary class to the exposed class. Position 4 is classified as an intermediate residue by the present invention's algorithm and as an exposed residue in D&M's work, and position 7 is classified as an exposed residue by the present invention's algorithm and as an intermediate in D&M's work.

1.2 The ββα Motif Optimization Process of the Energy Score Profile

Figure 2:
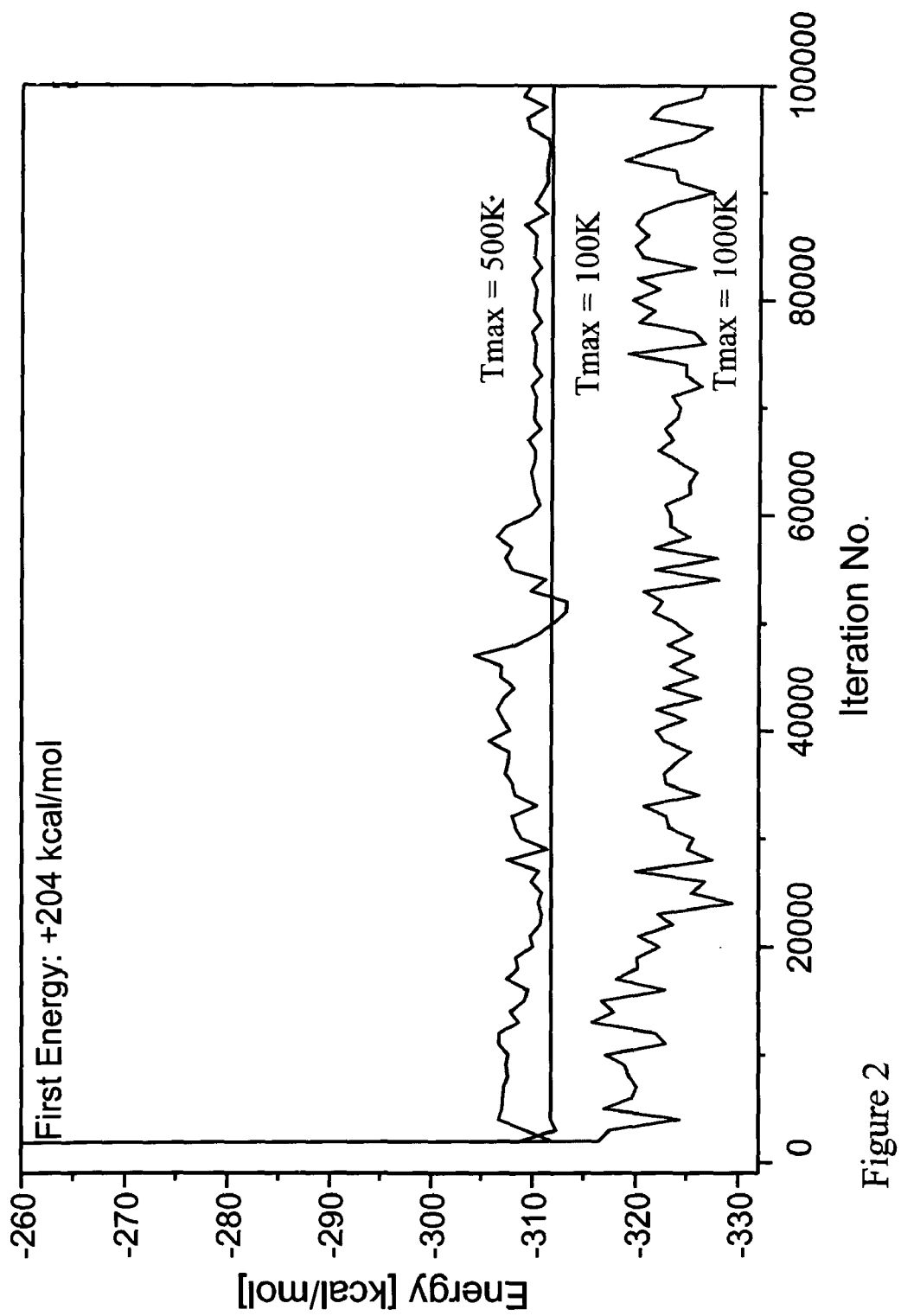
FIG. 2 shows the energy profile obtained for the Zin268 backbone by the system of the invention during $10^5$ iterations, at three maximal temperatures: 1000K (continuous line), 500K (broken line) and 100K (dotted line) using an annealing temperature profile, with periodicity of 500 Monte Carlo steps during which the temperature is gradually decreased from its initial value, to zero, and then set up again to its initial value for another cycle. The energy of the initial random sequence, before the simulation started was +204 kcal/mol.

A Monte Carlo (MC) search was conducted as described hereinbefore and the profile of the score as a function of MC trials is calculated. The results which depended on the temperature of the system, T, are presented in FIGS. 1 and 2. FIG. 1 presents the energy profile at three constant temperature parameters, 100K, 500K and 1000K. FIG. 2 presents the energy profile using an annealing profile of the temperature parameters. The maximal temperatures were also 100K, 500K and 1000K and the periodicity was 500 Monte Carlo steps. Namely, during each cycle of 500 MC steps the temperature parameter is gradually reduced until it reaches zero, at which point the temperature parameter is set again to its initial value for a new 500 step annealing cycle to begin. The total size of the search space was $3.41 \times 10^{43}$ but in all cases within less than 2000 iterations the algorithm reached the range of stable sequence between −270 kcal/mol and −300 kcal/mol, according to the scoring function.

It can be seen from FIGS. 1 and 2 that the optimization reaches lower scores when the periodic annealing temperature profile is used. This profile enables the program to escape local minima by accepting high-energy sequences that would not be accepted, but at the same time, to optimize locally when the temperature is reduced. Among the three temperatures examined, the search reached the lowest values for the scoring function initial temperature parameter was 1000K and an annealing profile was used.

Figure 3:
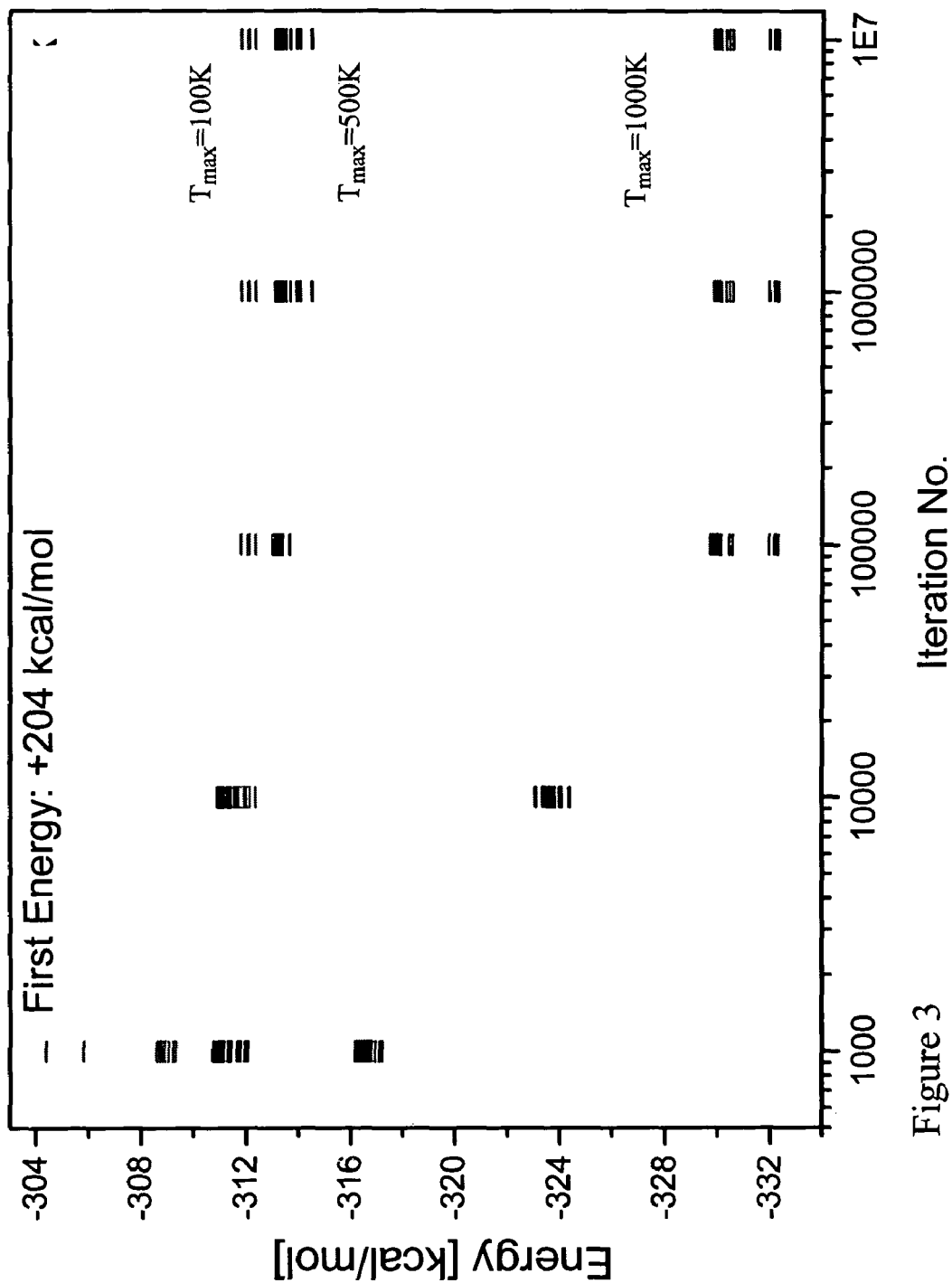
FIG. 3 shows the energies of the 20 lowest sequences generated by the algorithm at different simulation lengths and different temperatures, using an annealing temperature profile with periodicity of 500 Monte Carlo steps.

FIG. 3 shows the energies of the 20 lowest sequences generated by the algorithm with different simulation lengths and different temperatures, using an annealing temperature profile with a periodicity of 500 Monte Carlo steps. The results show that at 500K the algorithm converges after $10^6$ iterations, at 1000K after $10^5$ and at 100K after $10^4$ iterations and reached different energies each time.

The length of $10^6$ iterations of the zinc finger protein simulation required one CPU hour on a single alpha processor workstation, and about 1.5 hours on Pentium III PC.

TABLE 1

Solvent Accessibility of Zif268

| Residue No | | | | 5 | | | | 10 | | | | 15 | | | | 20 | | | | 25 | | | | | | | |
|---|---|---|---|---|---|---|---|---|---|---|---|---|---|---|---|---|---|---|---|---|---|---|---|---|---|---|---|
| 2nd Struct[1] | | E | E | E | | T | T | | E | E | E | | | H | H | H | H | H | H | H | H | H | H | H | | | |
| SEQ. ID NO. 1[2] | K | P | F | Q | C | R | I | C | M | R | N | F | S | R | S | D | H | L | T | T | H | I | R | T | H | T | G E |
| SA[3] | | e | e | i | i | b | e | e | e | e | e | e | i | e | e | e | e | e | i | e | e | i | i | e | e | i | e e |
| D&M's SA[4] | | e | e | i | e | b | e | i | e | e | e | e | i | e | e | e | e | e | i | e | e | i | i | e | e | i | e e |

[1] Secondary structure containing Extended sheet (E), Turn (T) or Helix (H);
[2] SEQ. ID NO. 1 corresponds to the Zif268 wild-type sequence written in one letter code;
[3] Solvent accessibility as determined by the invention, categorized as buried (b), exposed (e) or intermediate (i);
[4] Solvent accessibility as determined by Dahiyat and Mayo(13).

As may be seen from Table 1, there are only two differences in Zif268 solvent accessibility obtained by one embodiment of the present invention and by D&M, the latter employing the connolly algorithm [Connolly M. L. Science 221:709-713

1.3 Results of ββα Motif Design

A total number of 50 simulations of the program were performed, each one terminated after $10^6$ iterations under the same temperature conditions: an annealing temperature profile with an initial temperature of 1000K. Several different lengths of Monte Carlo steps periodicity were tested and it was found that the best annealing periodicity for a simulation of $10^6$ iteration was $10^4$ steps.

Each simulation began with a different random seed but, with the same 3D backbone template. The set of 50 simulations was repeated twice, each set with different solvent accessibility (SA) assignment for the protein residues. The first set used the present invention's automated solvent accessibility algorithm and the second set used Dahiyat and Mayo's (D&M) fitted assignments (see Table 1).

Tables 2A and 2B present the lowest energy sequences obtained in the first and second sets (A and B respectively), aligned with the second zinc finger module of the DNA binding protein Zif268 and with D&M designed sequence, FSD-1, SEQ. ID NO. 2. The coordinates used for the FSD-1 ββα motif score evaluations are the experimental NMR coordinates (PDB code 1FSD), which were found by D&M (13). All the energy scores in Table 2B were calculated according the method of the present invention's reduced representation of amino acids and its scoring function. A and B scores were found to be lower than both Zif268 score (without considering the His2Cys2 Zn-binding interactions which are not included in the scoring function), and the FSD-1 score. The energy score of the most stable sequence, A, corresponding to SEQ. ID NO 3, is −351.8 kcal/mol. This score is lower than Zif268 score by 111.3 kcal/mol which is a significant difference (not taking into account the Zn interactions). The relative stability of both SEQ. ID NO 3 and SEQ. ID NO 4 in comparison to SEQ. ID NO. 2, may be in part due to the fact SEQ. ID NO. 2 was designed with a different scoring function.

1.4 Analysis of the Resulting Sequence

Statistical calculations over the 50 sequences obtained in 50 simulations (data not shown) provide the following observations:

1. Even though all of the hydrophobic amino acids were allowed at the intermediate positions, the algorithm selected only non-polar amino acids at all those locations. This agrees well with the finding that these form a well-packed buried cluster [Dahiyat B. I. (1997), ibid.].
2. For positions 5, 8, 21, 25 of the original Zn-binding amino acids (two cysteines (C) and two histidines (H), the algorithm consistently selected residues of a well defined solvent accessibility character (even at "intermediate" positions). Hydrophobic amino acids (Val, Phe, Leu, Ile, and Met) were selected for positions 5, 21 and 25 which are classified as either "buried" or "intermediate". In the single exposed position (position 8), a hydrophilic amino acid was selected (His).
3. Positions 21 and 25 of the optimal sequences were selected to be Phe or Met (position 21) and Leu (position 25) side chains. In the original SEQ. ID NO. 1, these positions were occupied by the zinc binding His residue. These positions are more than 80 percent buried. Position 5, which is 100 percent buried, was predominantly selected to be Val. The other boundary positions demonstrate the steric constrains on buried residues by packing similar side chains to those of the original SEQ. ID NO. 1.
4. In the helix region (residues 15-26) the algorithm placed two Leu side chains and one Gln, which are good helix forming residues, in SEQ. ID NO. 4, and one Leu and one Gln in SEQ. ID NO. 3.

TABLE 2A

The most stable sequence obtained for the Zinc finger

| $2^{nd}$ struc.[1] | | E | E | E | | T | T | | E | E | E | | | H | H | H | H | H | H | H | H | H | H | H | H |
|---|---|---|---|---|---|---|---|---|---|---|---|---|---|---|---|---|---|---|---|---|---|---|---|---|---|---|
| SA[2] | | i | i | b | | | | | | | i | | | | i | | | i | i | | | | | | i | |
| D&M's SA[2] | | i | | b | | i | | | | | i | | | | i | | | i | i | | | | | i | | |
| Position | | | | 5 | | | | | | | 10 | | | | 15 | | | | 20 | | | | | 25 | | |
| SEQ. ID NO. 2[3] | Q | Q | Y | T | A | K | I | K | G | R | T | F | R | N | E | K | E | L | R | D | F | I | E | K | F | K | G | R |
| SEQ. ID NO. 1[4] | K | P | F | Q | C | R | I | C | M | R | N | F | S | R | S | D | H | L | T | T | H | I | R | T | H | T | G | E |
| SEQ. ID NO. 3[5] | E | H | M | F | V | H | H | H | T | T | R | F | S | S | H | T | S | F | T | S | F | L | R | S | M | Q | G | R |
| SEQ. ID NO. 4[6] | Q | H | M | T | V | H | F | H | N | T | T | F | S | H | H | S | S | L | S | T | F | L | Q | S | F | Q | G | R |

[1] Secondary structure containing Extended sheet (E), Turn (T) or Helix (H);
[2] Solvent Accessibility as determined by the invention, categorized as buried (b), exposed (e) or intermediate (i) (all other positions are exposed);
[3] The sequence as designed by D&M[13];
[4] SEQ. ID NO. 1 corresponds to wild-type Zif268 sequence written in one letter code;
[5] Sequence obtained by the present invention using the SA calculation described herein;
[6] Sequence obtained by the present invention using D&M SA fitted assignments.

TABLE 2B

Energy scores of the sequences presented in table 2A

| Sequence | Energy (kcal/mol) |
|---|---|
| FSD-1[1] | −166.5 |
| Wild type Zif268 (no $Zn^{2+}$) | −240.6 |
| A[2] | −351.9 |
| B[3] | −348.7 |

[1] The sequence designed by D&M[13];
[2] The sequence obtained by the present invention using SA calculations as described.
[3] The sequence obtained by the present invention using D&M SA fitted assignments.

5. In both SEQ. ID NO. 3 and SEQ. ID NO. 4, position 5 on the exposed sheet surface was selected by the algorithm to be Val, which is a very good β-sheet forming residue, and positions 4 and 10 (and 11 only in SEQ. ID NO. 4) were selected to be Thr, which is also a good β-sheet forming residue.
6. Alignment of the optimal stable SEQ. ID NO. 4 and SEQ. ID NO. 1 indicates that 4 out of 27 residues (not including residue 27 that remains Gly throughout the simulation) are identical (15%) and 11 are similar (including the identical 40.7%). D&M obtained similar values, with 5 identical residues (18.5%) and 12 similar (44.4%).

7. Alignment of the SEQ. ID NO. 4 and SEQ. ID NO. 2 indicates that 5 out of 27 residues are identical between the sequences (18.5%) and 11 are similar (including identical 40.7%).

7.1 Secondary structure prediction of the designed sequence SEQ. ID NO. 3 and SEQ. ID NO. 4 were further examined by secondary structure prediction by the SSPAL predictor at Sanger Centere [Salamov A. A. and Solovyev V. V. J. Mol. Biol. 247:11-15 (1995)], which enable to predict the secondary structure of a protein according to its primary structure (amino acid sequence). By these programs both SEQ. ID NO. 3 and SEQ. ID NO. 4 were predicted to have the desired Zinc finger motif. Table 3 presents the secondary structure of the native protein (Zif268) according to the Protein Data Bank (PDB), and SEQ. ID NO. 3 and SEQ. ID NO. 4 secondary structure prediction, according to SSPAL algorithm at Sanger Centre. SEQ. ID NO. 3 was predicted to have one α-helix (designated H) and two β-strands (designated E) (the ββα motif) while the predicted secondary structure to SEQ. ID NO. 4 contained only one α-helix and one β-strand.

1.5 Secondary Structure Prediction of the Designed Sequence

Sequence A and B were further examined by secondary structure prediction by the SSPAL predictor at Sanger Centere [Salamov A. A. and Solovyev V. V. J. Mol. Biol. 247:11-15 (1995)], which enable to predict the secondary structure of a protein according to its primary structure (amino acid sequence). By these programs both A and B sequences were predicted to have the desired Zinc finger motif. Table 3 presents the secondary structure of the native protein (Zif268) according to the Protein Data Bank (PDB), and A and B secondary structure prediction, according to SSPAL algorithm at Sanger Centre. A was predicted to have one α-helix (designated H) and two β-strands (designated E)(the ββα motif) while the predicted secondary structure to B contained only one α-helix and one β-strand.

and a 12 Å energy cutoff. The minimization included 200 steps of SD (Steepest Descent) and then additional 500 steps of ABNR (Adopted Basis Newton Raphson). After minimization, each of the three structures were embedded in an 18 Å water sphere which included ~1870 water molecules of type TIP3P [Jorgenes W. L. et al. J Chem. Phys. 79:926-935 (1983)]. Each of the water-protein systems of SEQ. ID NO. 3 and SEQ. ID NO. 4 were simulated for 500 ps at 300K (with a 16 Å energy cutoff) and a sample of 2000 conformations was collected from the resulting molecular dynamics trajectory. It was found that the secondary structure of the proteins was maintained during the molecular dynamic simulations.

The root-mean-square (rms) difference between the protein structure of the designed sequences before the molecular dynamics simulation and their protein structure after the molecular dynamics simulation was:

| Sequence: | Backbone: | Side Chains: | Total: |
|---|---|---|---|
| A | 1.84Å | 3.05Å | 2.69Å |
| B | 1.84Å | 2.71Å | 2.43Å |

These results clearly indicate that the overall fold of the designed proteins remained ββα with some relaxation of backbone and side chains.

The molecular mechanics average energies of the two protein sequences during the simulations were:

| | |
|---|---|
| A:- | −437.4 kcal/mol |
| B:- | −196 kcal/mol |

TABLE 3

Secondary structure of predicted primary structures A and B.

```
Position              5         10        15        20        25
SS(1)  PDB        E E E   T T   E E E     H H H H H H H H H H H
SEQ. ID NO. 1 K P F Q C R I C M R N F S R S D H L T T H I R T H T G E
SS(1)  A          E E E E         E E     H H H H H H H H H
SEQ. ID NO. 3 E H M F V H H H T T R F S S H T S F T S F L R S M Q G R
SS(1)  B          E E E E E E               H H H H H H H H
SEQ. ID NO. 4 Q H M T V H F H N T T F S H H S S L S T F L Q S F Q G R
```

(1)Secondary Structure 1.6 Molecular Dynamics of the Re-designed Sequences

The reduced representation of the lowest energy designed SEQ. ID NO. 3 and SEQ. ID NO. 4, was expanded to an all-atom representation, using the molecular mechanics package CHARMM. The input for this experiment was the backbone coordinates of the native protein, the new designed residues and the dihedral angles of each position along the designed sequence derived from the rotamer with the lowest energy score. The number of atoms of SEQ. ID NO. 3 and SEQ. ID NO. 4 after expansion to all atoms, were 459 and 446, respectively. Energy minimization was performed for SEQ. ID NO. 3 and SEQ. ID NO. 4 side chains as well as to SEQ. ID NO. 1 side chains using CHARMM forcefield, the SHAKE algorithm [Van Gunsteren W. F. & Berendsen H. J. C. Mol. Phys. 34:1311 (1977)], a dielectric constant of ϵ=1

The above energy results indicate that the method and system of the present invention is indeed useful for the prediction of primary sequences that stabilize the ββα motif even in the absence of the ion.

The differences between the energy scores calculated for sequences A and B by the scoring function of the present invention and by the CHARMM force-field (after dynamics) were only 20% and 44%, respectively, these results indicate that the scoring function of the present invention provides a satisfactory evaluation to the potential energy of the designed sequences. Furthermore, in both CHARMM force-field and the scoring function of the present invention, sequence A yielded a significantly more stable structure that sequence B.

For comparison of the zinc bound wild-type Zif268 was also simulated using a system of solvated Zif268 wherein only the water sphere was allowed to move, while the protein coordinates were kept fixed. The system was simulated for 100 ps at 300K and a sample of 400 conformations was collected from the resulting molecular dynamics trajectory. The average CHARMM energy for Zif268 was −1657.6 kcal/mol (Zn interaction with its four anchor residues contributing: ~298.719 kcal/mol. The reason for the great difference with respect to the Zif268 energy score by the function of the present invention compared to its CHARMM energy is that the scoring function calculation of the native protein does not consider the contribution of the $His^2Cys^2Zn$-binding interactions.

Figure 4A:
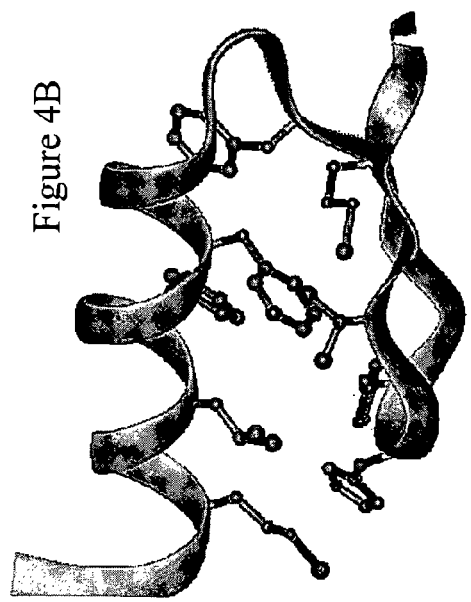
FIGS. 4A-4C shows the three dimensional structure crystallography of Zif268 (FIG. 4A) compared with the 3D structure of the designed proteins A and B (FIGS. 4B and 4C, respectively).
Figure 4B:
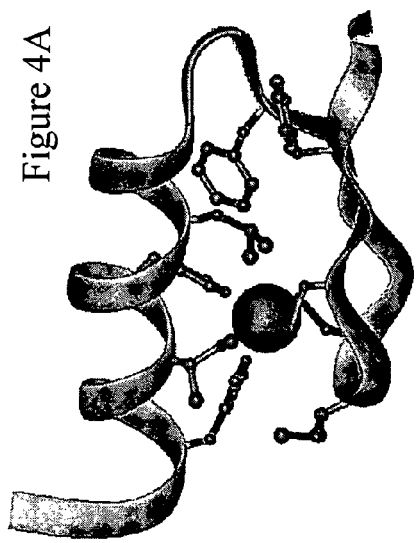
Figure 4C:
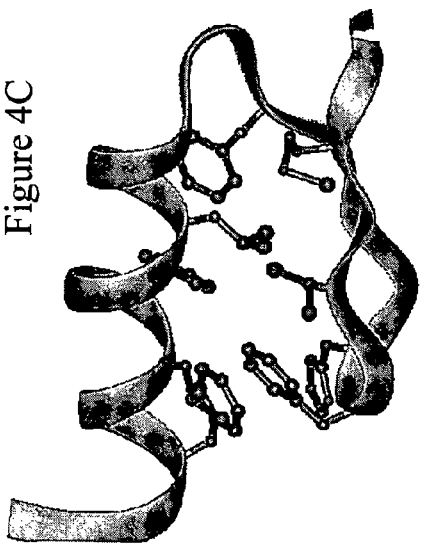
Figure 5A:
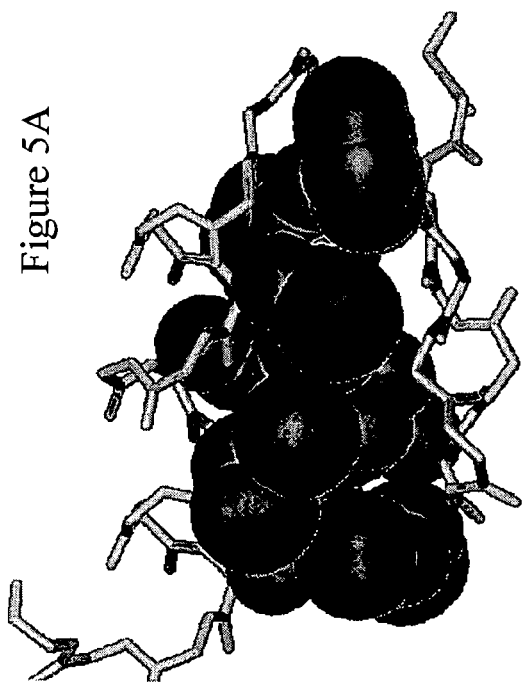
FIGS. 5A-5C shows the 3D crystallography structure of Zif268 (FIG. 5A) compared with the three dimensional structure of the designed proteins A and B (FIGS. 5B and 5C, respectively), after minimization of their side chains, displayed by spheres sized to the van der Walls radii of the atoms (not including hydrogens).
Figure 5B:
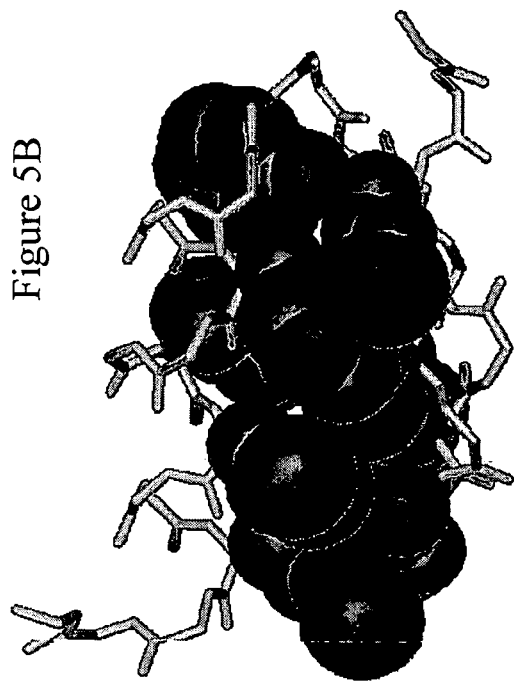
Figure 5C:
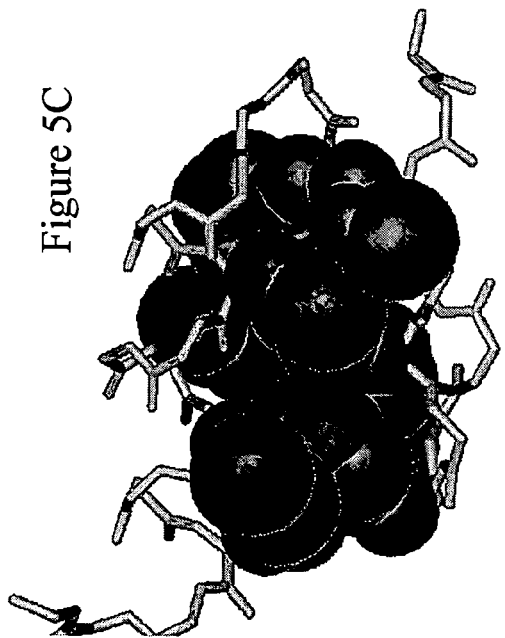

FIGS. 4A-4C show the 3D structure of Zif268 as compared to that of the designed proteins A and B after minimization of their side chains, focusing on the core, which includes hydrophobic side chains in A and B, instead of the zinc ion chelated by two cysteines and two histidines in the native protein. The same structures are presented in FIG. 5 but with the core side chains displayed by spheres sized to the van der Waals radii of the atoms, which indicate the good packing of the core in the designed sequences.

Example 2

Gβ1 as a Target Fold

The core of β1 domain of Streptococcal protein G (Gβ1), a 56 residue protein, was examined. Gβ1 is derived from a larger multi-domain cell surface protein that functions with high affinity binding to the Fc region of IgG. It comprises six β-strands and one α-helix. An extremely hyperthermophilic variant of the β1 domain of Streptococcal protein G was already reported by Mayo and collaborators[14,15].

2.1 Solvent Accessibility for Gβ1 Domain

Figure 6:
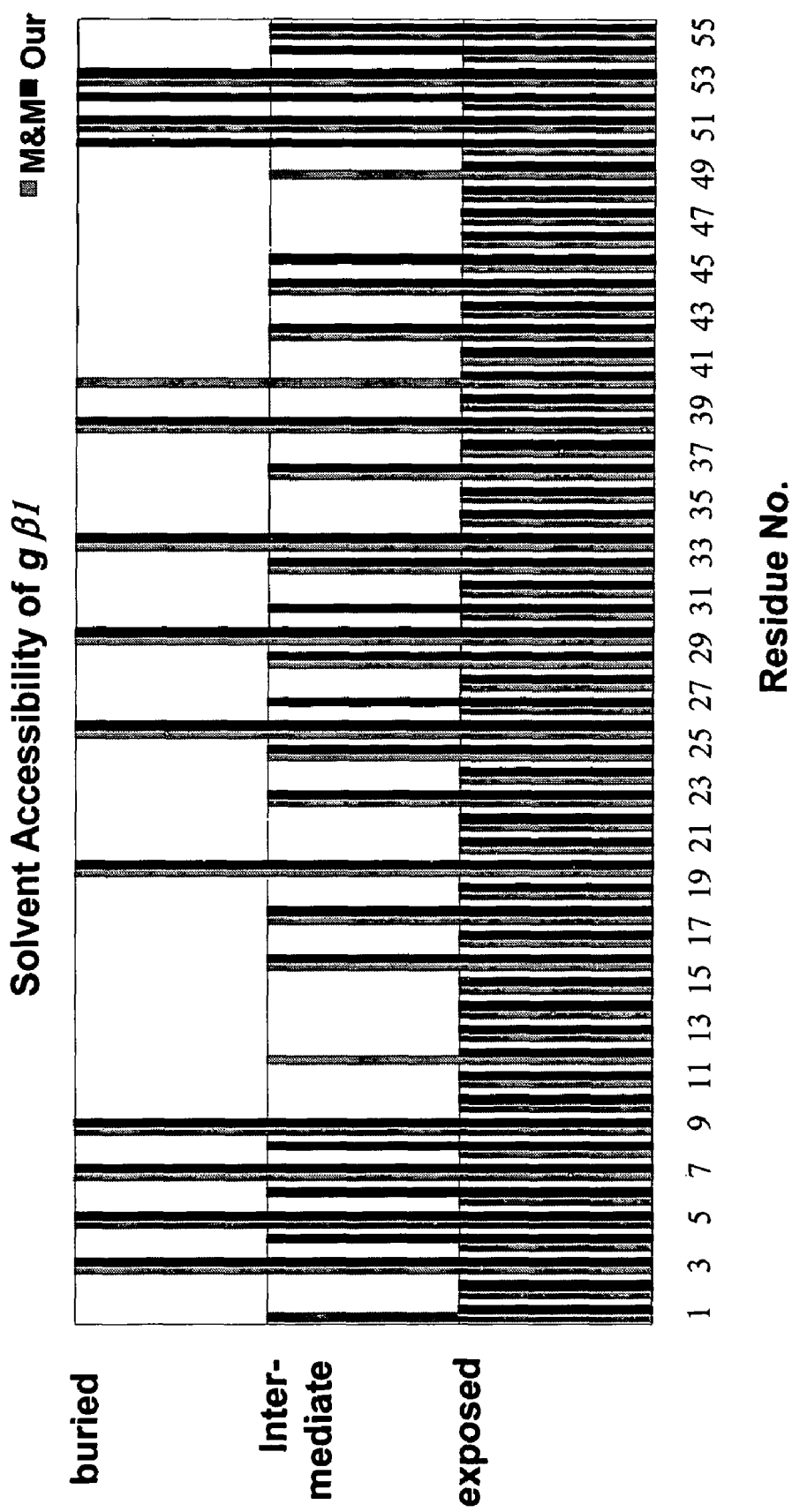
FIG. 6 shows a diagram of Gβ1 solvent accessibility, according to the present invention's methodology (black columns) and according to D&M (gray columns).

Solvent accessibility was evaluated as described in Example 1. A comparison of the results obtained by the method of the present invention and that of Malakauskas and Mayo (M&M[15], using mainly the Connolly algorithm referred to hereinbefore) is presented in FIG. 6. As can be seen from this Figure, 22 positions were found to be exposed in both cases, 11 were found to be buried and 10 in an intermediate level of solvent accessibility. The 13 remaining residues were classified differently in the two methods. In 10 of these cases the discrepancy was between the subtle definition of a site as being "buried" or "intermediate". The solvent accessibility of the eighth position (position 8) selected for optimization was identical in two classification schemes.

2.2 Results of Gβ1 Core Design

The energy score profile for Gβ1 was obtained by the same manner as described for Zif268. Further, the energy score profile obtained for Gβ1 was similar to that obtained for Zif268 (FIGS. 1 and 2), using the same temperature conditions. However, since only 8 out of 56 residues (14.3%) were mutated, the initial energy was already negative while the final energies obtained were approximately −770 and −790 kcal/mol when an annealing temperature profile was used and the maximal value for the temperature parameter was 1000K.

Two sets of 50 simulations were conducted. In the first set of simulations, the non-mutated positions were kept in their native rotameric conformation while in the second set of simulations, the rotameric states of the side chains of the non-mutating residues were allowed to change, thus providing a larger number or possible mutations and rotamer combinations. The total size of the search space in the first set was $1.06 \times 10^{13}$ and in the second set was $2.52 \times 10^{31}$. Each simulation in the first set was terminated after $10^4$ iterations with a maximal temperature of 1000K and an annealing periodicity of 100 MC steps. Each simulation in the second set was terminated after $10^5$ iterations, with a maximal temperature of 1000K and an annealing periodicity of 1000 MC steps.

Table 4 presents the mutated residues in the lowest energy sequences among the 50 simulations conducted for each set (C and D respectively).

TABLE 4

| 2nd structure[1] | E | E |   | E | H | H |   | E | Energy score[2] kcal/mol |
|---|---|---|---|---|---|---|---|---|---|
| Solvent accessibility | b | b | i | i | i | i | b | i |  |
| Position | 3 | 7 | 16 | 18 | 25 | 29 | 39 | 43 |  |
| SEQ. ID NO. 5 | Y | L | T | T | T | V | V | M | −676.4 |
| SEQ. ID NO. 6 | L | L | L | F | L | L | V | M | −778.6 |
| SEQ. ID NO. 6 | L | L | F | L | L | S | V | F | −788.8 |
| SEQ. ID NO. 8 | F | I | I | I | Q | I | I | I |  |

[1]E-β-sheet, H-helix;
[2]Energy score by the scoring function of the present invention
[3]Sequence designed by M&M[15]

2.3 Analysis of the Resulting Sequences

Statistical calculations over the 50 sequences obtained in 50 simulations in the fixed and non-fixed conformations, the latter having rotameric freedom (sets C and D, data not shown) provided the following observations:

1. In 72%-76% of the sequences buried positions 7 and 39 were found to be Leu and Val, respectively, as in the native protein.
2. In most sequences Thr25 was mutated to Leu, which has a better helix propensity. Examining of SEQ. ID NO. 6 and SEQ. ID NO. 7 by SSPAL predictor at Sanger Centre (as described hereinbefore) and by the PHD predictor at EMBL [Rost B and Sander C. J. Mol. Biol. 232:584-599 (1993)] showed that mutations T25L and V29L maintained the secondary structure of the α-helix.
3. More than 80% of the sequences consisted of the mutations T16L, T18L and T18F, which are located in a β-strand. The Leu and Phe apparently can substitute from the wild-type Thr without compromising the β-sheet propensity.
4. The buried position 3 changed from Tyr mainly to Leu, which is more hydrophobic and is predicted to improve side chain packing in the interior of the protein.
5. Four percent of the 50 sequences in the first simulation set, where the coordinates of the non-mutated residues were kept fixed, had Trp in position 43, the same as in the native protein. In the second simulation set, this position was predominantly assigned with Phe residue.

1.4 Minimization of the Redesigned Sequences in Comparison to Native Gβ1 of SEQ. ID NO. 5

The reduced representation of the designed SEQ. ID NO. 6, which was the sequence with the lowest energy score in the first set of simulations, where the conformation of 48 non-mutated residues was kept fixed, was expanded to its all-atom representation, using CHARMM [Brooks B. R. et al. (1983) ibid.], in the same manner as described hereinbefore. In general, the information provided as input was the backbone coordinates of the native protein, the new residues and the rotamer dihedral angles at each position along the chain. The number of atoms in SEQ. ID NO. 6 was 865. Energy minimization was performed for the side chains of this sequence as well as for Gβ1's side chains using CHARMM force-field [Mackerel A. D. et. Al. (1998) ibid.], a dielectric constant ε=1 and a 16 Å energy cutoff. The minimization included 800 steps of SD and then additional 1100 steps of ABNR. The average energies of the sequences after minimization were:

SEQ. ID NO. 5: −804.2 kcal/mol
SEQ. ID NO. 6: −822.7 kcal/mol

The above results suggest that the mutations obtained by the methodology disclosed herein are tolerable which may lead to the designed of a more stable protein.

The difference between the energies of the native sequence SEQ. ID NO. 5 and SEQ. ID NO. 6, based on the present invention's scoring function and on CHARMM's force-field (after dynamics) were 7% and 16% respectively, which strengthens the conclusion that the method and system of the present invention provide a reliable tool for designing de novo proteins.

Figure 7B:
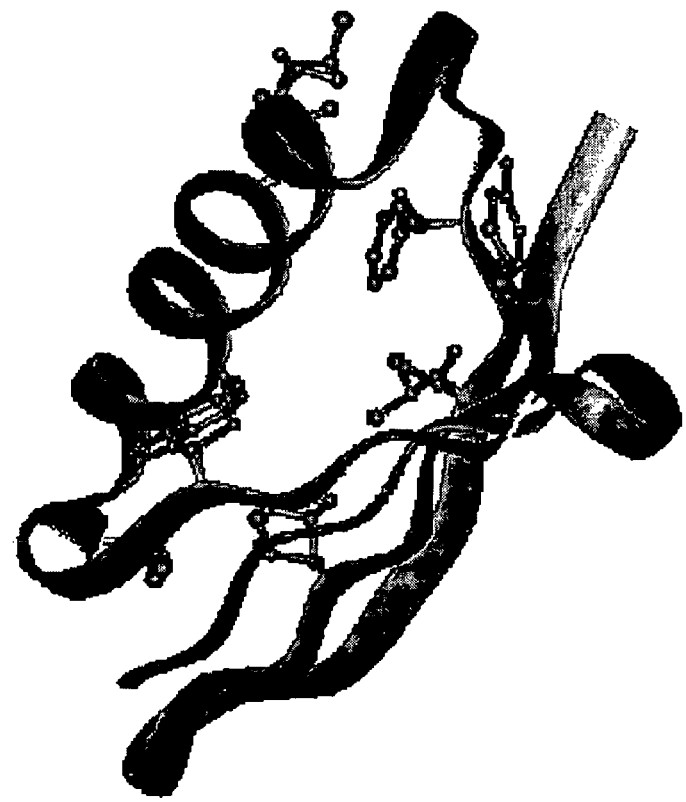
FIGS. 7A-7B shows the 3D structure of Gβ1 overlaid on that of the designed sequence C from two different angles (FIGS. 7A and 7B).
Figure 7A:

The above statement is further strengthened in light of FIG. 7, which show a comparison of the 3D structure of SEQ. ID NO. 5 and SEQ. ID NO. 6.

These results show that re-designing five boundary residues and three buried positions in the core of β1 domain of Streptococcal protein G was tolerable and that a stable, fully folded de novo protein may be obtained.

While the foregoing description disclosed in detail only a few specific embodiments of the invention, it will be understood by those skilled in the art that the method and system of the invention is not limited for the design of these proteins. Further, it should be understood that other variations of the method and system of the invention may be possible without departing from the scope and spirit of the invention as herein disclosed.

SEQUENCE LISTING

```
<160> NUMBER OF SEQ ID NOS: 8

<210> SEQ ID NO 1
<211> LENGTH: 28
<212> TYPE: PRT
<213> ORGANISM: Unknown
<220> FEATURE:
<223> OTHER INFORMATION: Zif268 wild-type sequence

<400> SEQUENCE: 1

Lys Pro Phe Gln Cys Arg Ile Cys Met Arg Asn Phe Ser Arg Ser Asp
1               5                   10                  15

His Leu Thr Thr His Ile Arg Thr His Thr Gly Glu
            20                  25

<210> SEQ ID NO 2
<211> LENGTH: 28
<212> TYPE: PRT
<213> ORGANISM: Artificial Sequence
<220> FEATURE:
<223> OTHER INFORMATION: FSD-1 - the sequence as designed by D&M.
      [Dahiyat BB.I. & Mayo S.I. Protein Sci. 5::895-903 (1997)]

<400> SEQUENCE: 2

Gln Gln Tyr Thr Ala Lys Ile Lys Gly Arg Thr Phe Arg Asn Glu Lys
1               5                   10                  15

Glu Leu Arg Asp Phe Ile Glu Lys Phe Lys Gly Arg
            20                  25

<210> SEQ ID NO 3
<211> LENGTH: 28
<212> TYPE: PRT
<213> ORGANISM: Artificial Sequence
<220> FEATURE:
<223> OTHER INFORMATION: Sequence obtained by the present invention
      using solvent accessibility (SA) calculation

<400> SEQUENCE: 3

Glu His Met Phe Val His His His Thr Thr Arg Phe Ser Ser His Thr
1               5                   10                  15

Ser Phe Thr Ser Phe Leu Arg Ser Met Gln Gly Arg
            20                  25

<210> SEQ ID NO 4
<211> LENGTH: 28
<212> TYPE: PRT
<213> ORGANISM: Artificial Sequence
<220> FEATURE:
<223> OTHER INFORMATION: Sequence obtained by the present invention
      using D&M (Dahiyat BB.I. & Mayo S.I. Protein Sci. 5::895-903
```

-continued (1997)) solvant accessibility (SA) fitted assignments

<400> SEQUENCE: 4

```
Gln His Met Thr Val His Phe His Asn Thr Thr Phe Ser His His Ser
1               5                   10                  15
Ser Leu Ser Thr Phe Leu Gln Ser Phe Gln Gly Arg
            20                  25
```

<210> SEQ ID NO 5
<211> LENGTH: 8
<212> TYPE: PRT
<213> ORGANISM: Unknown
<220> FEATURE:
<223> OTHER INFORMATION: Streptococcal protein G derived from a larger
      multi-domain cell surface protein that functions with high
      affinity binding to the Fc region of lgG

<400> SEQUENCE: 5

```
Tyr Leu Thr Thr Thr Val Val Trp
1               5
```

<210> SEQ ID NO 6
<211> LENGTH: 8
<212> TYPE: PRT
<213> ORGANISM: Artificial Sequence
<220> FEATURE:
<223> OTHER INFORMATION: mutuated residues in the lowest energy
      sequences kept in their native rotameric conformation

<400> SEQUENCE: 6

```
Leu Leu Leu Phe Leu Leu Val Met
1               5
```

<210> SEQ ID NO 7
<211> LENGTH: 8
<212> TYPE: PRT
<213> ORGANISM: Artificial Sequence
<220> FEATURE:
<223> OTHER INFORMATION: mutuated residues in the lowest energy
      sequences in which rotameric states of the side chains of the
      non-mutating residues were allowed to change

<400> SEQUENCE: 7

```
Leu Leu Phe Leu Leu Ser Val Phe
1               5
```

<210> SEQ ID NO 8
<211> LENGTH: 8
<212> TYPE: PRT
<213> ORGANISM: Artificial Sequence
<220> FEATURE:
<223> OTHER INFORMATION: Sequence designated by M&M. Nat.Struc. Biol.
      5:470-475 (1998)

<400> SEQUENCE: 8

```
Phe Ile Ile Ile Gln Ile Ile Ile
1               5
```

The invention claimed is:

1. A computer-implemented method for predicting at least one amino acid sequence that folds into a specified three-dimensional (3D) structure of a predetermined reference protein or peptide, the at least one amino acid sequence having a biological activity the same as a biological activity of the reference protein or peptide; which method comprises the steps of:

a) providing a coordinate set representing the backbone of the 3D structure;

b) constructing a reduced virtual representation for the 3D structure provided in step (a), wherein in the reduced representation, each amino acid has a backbone portion and a side chain portion, the backbone portion of each amino acid being represented by a single sphere and the side chain of each amino acid being represented by one to three additional spheres;

c) determining for each amino acid position along the virtual structure representation provided in step (b) its solvent accessibility;

d) constructing an initial amino acid sequence by assigning for each amino acid position along the structure an amino acid residue selected randomly from a predefined group of amino acids having a solvent accessibility compatible with the solvent accessibility of the position;

e) randomly selecting one or more positions along the sequence provided in step (d) and applying on each position a Monte-Carlo simulation in sequence space and rotamer space, the simulation comprising one or more scoring function calculating steps which include:
   i) randomly selecting one or more amino acid residues of the same solvent accessibility as that defined for the position to obtain a mutation;
   ii) for each of the one or more selected positions, calculating an energy difference delta E, between the amino acid residue at the position in the predetermined protein or peptide and each of the one or more selected amino acid residues provided in step (i) based on its reduced virtual representation;
   iii) selecting a rotamer having a minimal delta E, or when more than one amino acid are manipulated simultaneously, selecting a rotamer combination having a minimal delta E;
   iv) accepting the mutation with the rotamer or rotamer combination selected in step (iii) if delta E<0; and
   v) assigning the amino acid residue or residues and their respective selected rotamer or rotamer combinations selected in step (iii) to the position(s) and moving to another position along the sequence;
wherein the simulation steps are repeated until for each position along the sequence, the residue and residue's rotamer with the lowest energy score is selected, to obtain a virtually represented amino acid sequence with the lowest total energy score;

f) expanding the reduced representation of the virtually represented amino acid sequence obtained in step (e) to its corresponding all-atom sequence representation thereby obtaining an amino acid sequence compatible with the structure of the predetermined protein or peptide; and g) outputting the expanded all-atom representation of the amino acid sequence obtained in step (f), wherein at least steps (b)-(f) are preformed on a sufficiently programmed computer.

2. The method as claimed in claim 1, wherein the 3D structure provided in step (a) is that of a native peptide, or protein, or of a designed protein.

3. The method as claimed in claim 1, wherein the coordinate set is provided in a computer readable form.

4. The method as claimed in claim 1, wherein the amino acid sequence comprises naturally occurring amino acid residues, synthetic amino acid residues, or variations of the naturally occurring or synthetic amino acid residues.

5. The method as claimed in claim 1, wherein for each position along the 3D structure its solvent accessibility is determined according to the extent of exposure of the position to the solvent surrounding it, the position being either buried, exposed or intermediate position.

6. The method as claimed in claim 5, wherein the solvent is an aqueous solvent.

7. The method as claimed in claim 6, wherein the buried positions are occupied by hydrophobic amino acid residues.

8. The method as claimed in claim 7, wherein the hydrophobic amino acid residues are each independently selected from the group consisting of Ala, Tyr, Trp, Val, Leu, Ile, Phe, Met, Cys, Pro, and Gly.

9. The method as claimed in claim 5, wherein the exposed positions are occupied by hydrophilic amino acid residues.

10. The method as claimed in claim 9, wherein the hydrophilic amino acid residues are each independently selected from the group consisting of Lys, Arg, His, Glu, Asp, Gln, Asn, Ser, and Thr.

11. The method as claimed in claim 5, wherein the intermediate positions are occupied by either hydrophilic or hydrophobic amino acid residues.

12. The method as claimed in claim 11, wherein the intermediate positions are occupied by amino acid residues each being independently selected from the group consisting of Pro, Lys, Arg, His, Glu, Asp, Gln, Asn, Ser, Thr, Gly, Ala, Tyr, Trp, Val, Leu, Ile, Phe, Met, and Cys.

13. The method as claimed in claim 1, wherein the Monte Carlo simulation is applied simultaneously on up to three random positions in the sequence.

14. The method as claimed in claim 1, wherein the Monte Carlo step is conduced either at a fixed temperature or at a varying annealing temperature.

15. The method as claimed in claim 1, wherein a de novo amino acid sequence is generated.

16. The method as claimed in claim 1, wherein the amino acid sequence folds under physiological condition into a biologically functional 3D conformation substantially identical to the structure of the predetermined protein or peptide or to a portion thereof.

17. The method as claimed in claim 15, wherein the de novo amino acid sequence stabilizes the 3D structure, as compared to a native amino acid sequence.

18. An amino acid sequence which folds under physiological conditions into a specified 3D structure, said amino acid sequence is obtained by the method of claim 1.

19. The method as claimed in claim 16, wherein the de novo amino acid sequence stabilizes the 3D structure, as compared to a native amino acid sequence.

20. The method as claimed in claim 1, wherein the method does not utilize the dead-end elimination algorithm to eliminate rotamers that are mathematically provable to be inconsistent with a global minimum energy solution of a system.

21. A computer-implemented method for predicting at least one amino acid sequence that folds into a specified three-dimensional (3D) structure of a predetermined reference protein or peptide, the at least one amino acid sequence having a biological activity the same as a biological activity of the reference protein or peptide; consisting of:

a) providing a coordinate set representing the backbone of the 3D structure;

b) constructing a reduced virtual representation for the 3D structure provided in step (a), wherein in the reduced representation, each amino acid has a backbone portion and a side chain portion, the backbone portion of each amino acid being represented by a single sphere and the side chain of each amino acid being represented by one to three additional spheres;

c) determining for each amino acid position along the virtual structure representation provided in step (b) its solvent accessibility;
d) constructing an initial amino acid sequence by assigning for each amino acid position along the structure an amino acid residue selected randomly from a predefined group of amino acids having a solvent accessibility compatible with the solvent accessibility of the position;
e) randomly selecting one or more positions along the sequence provided in step (d) and applying on each position a Monte-Carlo simulation in sequence space and rotamer space, the simulation comprising one or more scoring function calculating steps which include:
  i) randomly selecting one or more amino acid residues of the same solvent accessibility as that defined for the position to obtain a mutation;
  ii) for each of the one or more selected positions, calculating an energy difference delta E, between the amino acid residue at the position in the predetermined protein or peptide and each of the one or more selected amino acid residues provided in step (i) based on its the reduced virtual representation;
  iii) selecting a rotamer having a minimal delta E, or when more than one amino acid are manipulated simultaneously, selecting a rotamer combination having a minimal delta E;
  iv) accepting the mutation with the rotamer or rotamer combination selected in step (iii) if delta E<0; and
  v) assigning the amino acid residue or residues and their respective selected rotamer or rotamer combinations selected in step (iii) to the position(s) and moving to another position along the sequence;

wherein the simulation steps are repeated until for each position along the sequence, the residue and residue's rotamer with the lowest energy score is selected, to obtain a virtually represented amino acid sequence with the lowest total energy score;

f) expanding the reduced representation of the virtually represented amino acid sequence obtained in step (e) to its corresponding all-atom sequence representation thereby obtaining an amino acid sequence compatible with the structure of the predetermined protein or peptide; and
g) outputting the expanded all-atom representation of the amino acid sequence obtained in step (f), wherein at least steps (b)-(f) are preformed on a sufficiently programmed computer.

* * * * *